United States Patent [19]

Mitra et al.

[11] Patent Number: 5,332,429
[45] Date of Patent: Jul. 26, 1994

[54] METHOD FOR TREATING FLUOROALUMINOSILICATE GLASS

[75] Inventors: Sumita B. Mitra, West St. Paul; Scott R. Culler, Burnsville; Bing Wang, Maplewood, all of Minn.

[73] Assignee: Minnesota Mining and Manufacturing Company, St. Paul, Minn.

[21] Appl. No.: 887,619

[22] Filed: May 22, 1992

Related U.S. Application Data

[63] Continuation-in-part of Ser. No. 708,467, May 31, 1991, abandoned.

[51] Int. Cl.$^5$ .......................... A61K 5/00; C03C 17/00
[52] U.S. Cl. .......................... 106/35; 65/60.3; 65/60.8; 427/212
[58] Field of Search ............. 65/60.8, 60.3; 106/35; 427/212–218

[56] References Cited

U.S. PATENT DOCUMENTS

| | | | |
|---|---|---|---|
| 3,539,533 | 6/1968 | Lee, II. et al. | 105/35 |
| 3,655,605 | 4/1972 | Smith et al. | 260/29.6 |
| 3,814,717 | 6/1974 | Wilson et al. | 260/29.6 |
| 4,016,124 | 4/1977 | Crisp et al. | 260/29.6 |
| 4,043,327 | 8/1977 | Potter et al. | 128/89 |
| 4,143,018 | 3/1979 | Crisp et al. | 260/29.6 |
| 4,209,434 | 6/1980 | Wilson et al. | 260/29.6 |
| 4,217,264 | 8/1980 | Mabie et al. | 260/42.15 |
| 4,250,277 | 2/1981 | Maries et al. | 525/337 |
| 4,376,835 | 3/1983 | Schmitt et al. | 523/116 |
| 4,652,593 | 3/1987 | Kawahara et al. | 523/116 |
| 4,673,354 | 6/1987 | Culler | 433/217.1 |
| 4,872,936 | 10/1989 | Engelbrecht | 156/307.3 |
| 4,940,607 | 7/1990 | Culler et al. | 427/140 |
| 5,063,257 | 11/1991 | Akahane et al. | 523/116 |

FOREIGN PATENT DOCUMENTS

| | | | |
|---|---|---|---|
| 0182924 | 6/1986 | European Pat. Off. | C08F 8/42 |
| 0199445 | 10/1986 | European Pat. Off. | C08F 8/42 |
| 0235526 | 9/1987 | European Pat. Off. | C08F 8/42 |
| 0323120 | 7/1989 | European Pat. Off. | A61K 6/08 |
| 0345961 | 12/1989 | European Pat. Off. | C08K 5/54 |
| 2640503 | 6/1990 | France | A61K 6/083 |

OTHER PUBLICATIONS

Chemical Abstracts, vol. 105, No. 9 Nov. 1986, abstract No. 154812q.
Chemical Abstracts, vol. 107, No. 2 Jul. 1987, abstract No. 11806w.
Patent Abstracts of Japan, vol. 6, No. 106 (C-108) 16 Jun. 1982.

*Primary Examiner*—Paul Lieberman
*Assistant Examiner*—Margaret Einsmann
*Attorney, Agent, or Firm*—Gary L. Griswold; Walter N. Kirn; F. Andrew Ubel

[57] ABSTRACT

Fluoroaluminosilicate dental cement glasses are treated with an aqueous silanol treating solution and optionally with an additional organic compound. The treated glasses form cements with improved strength. The silanol can be ethylenically-unsaturated and can contain acidic groups, and, if so, is novel in its own right.

37 Claims, No Drawings

METHOD FOR TREATING FLUOROALUMINOSILICATE GLASS

CROSS-REFERENCE TO RELATED APPLICATION

This application is a continuation-in-part of U.S. patent application Ser. No. 07/708,467, filed May 31, 1991 now abandoned.

TECHNICAL FIELD

This invention relates to fluoroaluminosilicate glasses and to glass ionomer cements.

BACKGROUND ART

In recent years, fluoroaluminosilicate ("FAS") glass cements, also known as "glass ionomer cements", have become widely used in dentistry. They are fluoride-releasing and therefore cariostatic. However, they are also relatively fragile, as manifested by their low diametral tensile strength ("DTS") and low fracture toughness ("$K_{1c}$"). Glass ionomer cements are widely accepted for low stress applications such as liners and bases, but are prone to early failure in restorative applications, core build-ups and other high stress applications. This has tended to limit clinical use of these otherwise meritorious cements.

U.S. Pat. No. 5,063,257 describes glass ionomer cements containing a polymerizable unsaturated organic compound. In several examples of the '257 patent (e.g., examples 6–8 and 14–16), the fluoroaluminosilicate glass is treated with an anhydrous alcoholic solution of an ethylenically-unsaturated alkoxysilane. The resultant silane-coated glass is dried and later mixed with a polyacrylic acid and a methacrylate monomer. The '257 patent mentions but does not exemplify treating the glass with unsaturated carboxylic acids such as methacrylic acid, acrylic acid and maleic acid.

U.S. Pat. No. 4,250,277 describes a cement made from a treated aluminoborate glass. The treatment involves washing the glass with ammonium phosphate, in order to extend the setting time of the cement.

U.S. Pat. No. 4,376,835 describes a calcium aluminum fluorosilicate glass that has been treated with an acid. The treatment is said to reduce water sensitivity and extend setting time.

U.S. Pat. No. 4,652,593 describes a metal oxide cement containing a mixture of calcium oxide and aluminum oxide. The oxide powders are coated with a water-soluble high molecular weight substance. The coating is said to increase crushing strength, hydrophilicity and working time, and to decrease solubility.

U.S. Pat. No. 4,808,288 describes glass ionomer cement powders made by vigorous comminution of a glass and a carboxylic acid. The powders contain carboxylate groups.

European Published Patent Application 0 323 120 and U.S. Pat. No. 4,872,936 describe photocurable cements. The '936 patent describes silane-treating an optional added filler (e.g., microfine silica) but not a glass ionomer powder.

U.S. Pat. No. 4,673,354 describes silanol solutions that can be used to prime dental porcelains and dental alloys.

SUMMARY OF THE INVENTION

We have found that by treating the fluoroaluminosilicate glass with a silanol, substantially improved glasses can be obtained. The treated glasses are easily mixed with aqueous polyacrylic acid solutions, have excellent fluoride release, and provide cements with improved DTS and improved fracture toughness.

In our procedure, we adjust the treatment solution with an acid or base to provide a non-neutral solution (or we employ a silane that is not only ethylenically-unsaturated but also acid- or base-functional) and we carry out the treatment in the presence of water. Accordingly, the silane is converted to a silanol. The acid or base and the silanol react with the glass, and an improved treated glass is obtained. The treated glass may optionally be treated with an additional organic compound or mixture of compounds to further enhance strength and fracture toughness. Thus the present invention provides, in one aspect, a method for treating fluoroaluminosilicate glass, comprising the steps of:

a. mixing finely-divided fluoroaluminosilicate glass with an aqueous silanol solution, optionally borne in a volatile solvent, b. drying the glass, and optionally c. further mixing the dried silanol treated fluoroaluminosilicate glass with a solution of an additional organic compound or mixture of organic compounds, optionally borne in a volatile solvent, drying the treated glass, if necessary, to remove the volatile solvents therefrom, to provide an essentially dry powder blend of additional organic compound and silanol treated fluoroaluminosilicate glass or a viscous paste of additional organic compound and silanol treated fluoroaluminosilicate glass.

The invention also provides preferred novel treated fluoroaluminosilicate glasses, comprising a reactive organoaluminosilicate particulate glass having an ethylenically-unsaturated carboxylate ion-containing, siloxy-containing coating.

In addition, the invention provides novel monomeric, oligomeric and polymeric alkoxysilanes containing a backbone bearing ethylenically-unsaturated groups and carboxylic acid groups, the backbone being joined to the alkoxysilane via an amide group.

The treated glasses of the invention can be formulated into cements having outstanding physical properties and broad clinical applicability.

DETAILED DESCRIPTION

Briefly, the method of the invention involves mixing a finely-divided fluoroaluminosilicate glass with an aqueous silanol treating solution. A wide variety of fluoroaluminosilicate glasses can be treated. These glasses are well known in the art, and include glasses such as those described in U.S. Pat. Nos. 3,655,605, 3,814,717, 4,043,327, 4,143,018, 4,209,434 and 5,063,257. The glass preferably contains sufficient leachable fluoride to provide useful cariostatic protection when a cement made from the glass is placed in the mouth. The glass preferably is sufficiently finely divided to provide easy mixing, rapid cure and good handling properties in dental applications. Any convenient pulverizing or comminuting means can be employed to produce finely-divided glass. Ball-milling is a convenient approach.

The starting silanes utilized to fore the silanol treating solution can be ionic or nonionic or a combination thereof and can be monomeric, oligomeric or polymeric. Ionic silanes include anionic, cationic and zwitterionic silanes. Acidic or basic silanol treatment solutions can be prepared using ionic or nonionic silanes. Acidic ethylenically-unsaturated nonionic treatment solutions are most preferred. Although silanols are preferred for use in the present invention, the hydrolysis products of titanales or zirco-aluminates can, if desired, be used in addition to or instead of silanes.

Ionic starting silanes that can be utilized to form the silanol treatment solution include "T2909.7" N-(3-trimethoxysilylpropyl)-N-methyl-N,N-diallyl ammonium chloride, "T2921" trimethoxysilylpropylisothiouronium chloride, "T2924" N-trimethoxysilylpropyltributylammonium bromide and "T2925" N-trimethoxysilylpropyl-N,N,N-trimethylammonium chloride from Petrarch Chemical Co., Inc. A particularly preferred ionic silane is "T2909.7".

Nonionic silanes useful in the practice of the invention include "A-1100" gamma-aminopropyltriethoxysilane from Union Carbide Corp. and those listed in Column 5 lines 1–17 of U.S. Pat. No. 4,673,354. A preferred nonionic silane is gamma-methacryloxypropyltrimethoxysilane.

The acidic or basic aqueous silanol treating solution contains a monomeric, oligomeric or polymeric silanol. The acid or base in the treating solution can be home on the silanol, home on the silane, present as a separate component or combinations thereof. The treating solution is conveniently produced by dissolving a monomeric, oligomeric or polymeric alkoxy silane in a volatile solvent and water. Sufficient acid or base should be added to the solution or home on the silane to promote hydrolysis of the silane to a silanol.

A preferred treatment solution is an acidic aqueous silanol treating solution containing a monomeric, oligomeric or polymeric ethylenically-unsaturated silanol. The acid in the treating solution can be borne on the silanol, borne on the silane or present as a separate component. The treating solution is conveniently produced by dissolving a monomeric, oligomeric or polymeric ethylenically-unsaturated alkoxysilane in a volatile solvent and water. Sufficient acid should be added to the solution or borne on the alkoxysilane to promote hydrolysis of the alkoxysilane to a silanol.

The preferred treatment solution may optionally also contain an additional organic compound or mixture of compounds independently having at least one polymerizable, ethylenically unsaturated double bond and an average molecular weight of all species used to treat the fluoroaluminosilicate glass of up to about 5,000 units per double bond, wherein the molecular weight of each species is the weight average molecular weight evaluated against a polystyrene standard using gel permeation chromatography. More preferably, the average molecular weight of all species per double bond is between about 100 and 2,500 and most preferably between about 250 and 1,000. A preferred amount of additional organic compound is up to about 50 weight %, more preferably about 5 to 30 weight % and most preferably about 10 to 20 weight %, based on the total weight of the cement mixture. Treatment of the fluoroaluminosilicate glass with the additional organic compound or mixture of compounds may be concurrent or sequential with the silanol treatment. Preferably, treatment of the fluoroaluminosilicate glass with the additional organic compound follows treatment of the glass with the silanol.

The alkoxysilane preferably contains one or more hydrolyzable alkoxy groups, one or more pendant ethylenically-unsaturated groups, and optionally one or more pendant carboxylic acid groups. Suitable monomeric alkoxysilanes are conveniently prepared by reacting an ethylenically-unsaturated compound containing an active hydrogen group with an alkoxysilane containing an electrophilic group. A particularly preferred alkoxysilane is an isocyanato-functional alkoxysilane. Suitable ethylenically-unsaturated compounds include acrylic, methacrylic, maleic, itaconic, citraconic, and aconitic acids. Other suitable ethylenically-unsaturated compounds include 2-hydroxyethylmethacrylate, 2-hydroxypropylmethacrylate, acrylamide, methacrylamide, n-allyl amine and styryl benzyl amine. The ethylenically-unsaturated compound preferably contains at least one (and preferably two or more) carboxylic acid groups. The reaction with the isocyanato-functional alkoxysilane preferably is carried out at less than stoichiometric equivalence of carboxylic acid groups to isocyanato groups, so that the resulting ethylenically-unsaturated alkoxysilane bears residual unreacted carboxylic acid groups. Suitable isocyanato-functional alkoxysilanes include isocyanotoethyltrimethoxysilane, isocyanatopropyltrimethoxysilane, and isocyanatopropyltriethoxysilane.

Suitable polymeric alkoxysilanes are conveniently prepared by reacting an isocyanato-functional alkoxysilane of the type described above with a precursor polymer having pendant ethylenically-unsaturated groups and active hydrogen groups along its backbone. Preferably at least some of the active hydrogen groups in the precursor polymer are carboxylic acid groups, present in sufficient stoichiometric excess so that some of the carboxylic acid groups will remain after reaction with the isocyanato-functional alkoxysilane.

Preferred precursor polymers containing both ethylenically-unsaturated groups and carboxylic acid groups are described in European Published Patent Application No. 0 323 120. These can be reacted with an isocyanato-functional alkoxysilane to provide a particularly preferred class of novel ethylenically-unsaturated monomeric, oligomeric and polymeric alkoxysilanes having the formula:

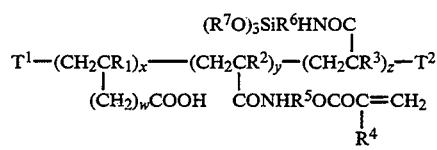

wherein $R^1$, $R^2$, $R^3$ and $R^4$ are independently H, $CH_3$, COOH or $CH_2COOH$; $R^5$ and $R^6$ are independently divalent alkylene linking groups; each $R^7$ is independently an alkyl group; $T^1$ and $T^2$ are independently terminating groups such as H or alkyl; w is 0 to 12; and each of x, y and z is at least one. Preferably $R^5$ is $C_2H_4$, $R^6$ is $C_3H_6$, $R^7$ is $CH_3$ or $C_2H_5$, $T^1$ and $T^2$ are H or $CH_3$, and w is 0 to 6.

Suitable additional organic compounds for treating the glass or filler include monomers, oligomers or polymers. If the additional organic compound is a monomer then the monomer may be monofunctional (i.e., containing only one ethylenically unsaturated double bond) or multifunctional (i.e., containing two or more double bonds). Presently preferred monomers are multifunctional with the presently most preferred monomers containing two double bonds.

If the additional organic compound is a polymer then the polymer may be a linear, branched or cyclic polymer of ethylenically unsaturated monomers or it can be polymeric compound like polyester, polyamide, polyether, polyethyleneglycol, polysaccharide, cellulosic, polyproplylene, polyacrylonitsile, polyurethane, poly(vinyl chloride), poly(methyl methacrylate), phenol-formaldehyde, melamine-formaldehyde, and urea-formaldehyde.

Presently preferred additional organic compounds contain both ethylenically-unsaturated groups (e.g., acrylate, methacrylate, alkene or acrylamide groups which are capable of further hardening reaction, i.e., crosslinking or copolymerizing with themselves or other components of the cement mixture) and hydrophilic groups (e.g., ethyleneoxy groups, alcohol groups and esters). Hydrophilic groups on the additional organic compounds may aid in dispersing the organic compound in the treatment solution when applying the treatment to the glass, and also may aid in the dispersability of the glass in the cement-forming liquid. It will be understood that these benefits may be present in mixtures of additional organic compounds when one compound has no or few hydrophilic groups and another compound has many hydrophilic groups. Preferred additional organic compounds contain ethyleneglycol groups.

Examples of suitable additional organic compounds include mono-, di- or polyfunctional acrylates and methacrylates such as methyl acrylate, methyl methacrylate, ethyl acrylate, isopropyl methacrylate, n-hexyl acrylate, styryl acrylate, allyl acrylate, glycerol diacrylate, glycerol triacrylate, ethyleneglycol diacrylate, diethyleneglycol diacrylate, triethyleneglycol dimethacrylate ("TEGDMA"), tetraethyleneglycol dimethacrylate, polyethyleneglycol dimethacrylate (e.g., "$PEG_{200}DMA$", "$PEG_{400}DMA$" and "$PEG_{600}DMA$" with an average of 4.5, 9 and 13.6 ethyleneglycol groups or "units" respectively), 1,3-propanediol diacrylate, 1,3-propanediol dimethacrylate, trimethylolpropane triacrylate, 1,2,3-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, trishydroxyethylisocyanurate triacrylate, beta-methacrylaminoethyl methacrylate, 2,2-bis[4-(2-hydroxy-3-methacryloyloxy-propoxy)phenyl]propane ("BIS-GMA"), 2,2-bis[4-(2-methacryloyloxyethoxy)-phenyl]propane, 2,2-bis[4-methacryloyloxyphenyl]propane, "SARTOMER" 350 ("SR350", Sartomer Corp.) and mixtures thereof. Other suitable monomers include unsaturated amides such as 2-acrylamidoglycolic acid, methylene bis-acrylamide, methylene bis-methacrylamide, 1,6-hexamethylene bis-acrylamide, tetra acrylamido glycuril ("TAGU") and diethylenetriamine tris-acrylamide. Suitable oligomeric or polymeric resins include up to 5000 molecular weight polyalkylene glycols, acrylated or methacrylated oligomers such as those of U.S. Pat. No. 4,642,126, acrylated urethanes such as "SARTOMER" 9503, 9504 and 9505 (Sartomer Corp.), "INTEREZ" CMD 8803, 8804 and 8805 (Radcure Specialties, Inc.), and "PHOTOMER 6060, 6110 and 6160 (Henkel Corp.), as well as acrylated polyester oligomers such as "EBERCRYL" 830 (Radcure Specialties, Inc.). Mixtures of free-radically polymerizable monomers, oligomers or polymers can be used if desired.

Examples of presently preferred additional organic compounds include mono-, di- or polyfunctional acrylates and methacrylates such as ethyleneglycol diacrylate, diethyleneglycol diacrylate, triethyleneglycol dimethacrylate, tetraethyleneglycol dimethacrylate, polyethyleneglycol dimethacrylate (e.g., "$PEG_{200}DMA$", "$PEG_{400}DMA$" and "$PEG_{600}DMA$" with an average of 4.5, 9 and 13.6 ethyleneglycol groups or "units" respectively), BIS-GMA, "SARTOMER" 350 and mixtures thereof. Other presently preferred monomers include unsaturated amides such as tetra acrylamido glycuril. Presently preferred oligomeric or polymeric resins include up to 5000 molecular weight polyalkylene glycols.

Presently most preferred additional organic compounds include triethyleneglycol dimethacrylate, tetraethyleneglycol dimethacrylate, "$PEG_{200}DMA$", BIS-GMA, "SARTOMER" 350, tetra acrylamido glycuril and mixtures thereof.

As mentioned above, the silanol treating solution contains the monomeric, oligomeric or polymeric silanol, water and an optional volatile solvent. The silanol should be present in the treating solution in an amount sufficient to increase by more then the experimental error of measurement the DTS of a glass ionomer cement made from a reactive powder treated with the solution. A preferred aamount of silanol in the treating solution is from about 0.1 to about 20 weight %, more preferably about 0.5 to about 10 weight %, based on the total weight of the treating solution.

The water in the treating solution facilitates hydrolysis of the silane. In order to discourage premature solution condensation of the silanol, the water preferably is substantially free of fluoride and other contaminants. Deionized water is preferred. Preferred aamounts of water are about 20 to about 99.9%, more preferably about 30 to about 95%, based on the total weight of the treating solution.

The acid or base in the treating solution should be capable of promoting hydrolysis of the silane to a silanol. Preferably the acid or base is borne on the silane. If present as a separate ingredient, the acid or base can be water-soluble and organic or inorganic. Preferred acids include formic acid, acetic acid, trifluoroacetic acid, propionic acid, pentafluoropropionic acid, hydrochloric acid, nitric acid, sulfuric acid, phosphoric acid, lactic acid, citric acid, and tartaric acid. Acetic acid is a particularly preferred separate acid. Preferred bases include sodium hydroxide, ammonium hydroxide, potassium hydroxide, barium hydroxide, lithium hydroxide, magnesium hydroxide, calcium hydroxide, sodium bicarbonate, ammonia, methylamine, dimethylamine, trimethylamine, ethylamine, diethylamine, n-propylamine, n-butylarnine, isobutylamine, sec-butylamine, and tert-butylamine. Sodium hydroxide is a particularly preferred separate base. Quaternary ammonium salts that hydrolyze to provide an acidic or basic solution can also be used. Such quaternary ammonium salts include ammonium bromide, ammonium chloride, isothiouronium bromide and isothiouronium chloride.

The amount of acid or base should, as noted above, be sufficient to promote hydrolysis of the silane. The desired aamount of acid or base can conveniently be monitored by measuring the pH of the treating solution. A preferred acidic pH is 5 or less, more preferably about 1 to about 4.5, and most preferably about 3 to about 4. A preferred basic pH is 8 or higher, more preferably about 9 to about 12, and most preferably about 9 to 11.

The optional volatile solvent in the treating solution serves to dissolve the silane and to aid in formation of a thin film of the treating solution on the finely-divided glass. Alcohol and ketone solvents are preferred. Methanol, ethanol, propanol, isopropanol, tert-butanol and acetone are particularly preferred solvents. Most preferably, the solvent is an alcohol, such as the alcohol formed by hydrolysis of, for example, an alkoxysilane. Methanol is thus a preferred solvent for methoxysilanes, and ethanol is a preferred solvent for ethoxysilanes.

When used, the aamount of solvent should be at least sufficient to dissolve the silane and form a homogeneous single-phase solution. A preferred aamount of solvent is about 40 weight % or more, with amounts between about 40 and 60 weight % being most preferred.

The solvent can be omitted by carrying out hydrolysis of the silane using vigorous stirring and continuous addition of the ingredients. The silane generally has poor water solubility, but the silanol has good water solubility and preferentially will be extracted into the water.

The ingredients in the treating solution are prepared by mixing them in any convenient order. Ordinarily, the water (and acid or base if present as a separate ingredient) are combined with the solvent and the silane. The resulting mixture is stirred for a time sufficient to promote hydrolysis of the silane, and then preferably used before the onset of haziness (which indicates undesirable condensation of the silanol).

The finely-divided glass and treatment solution, optionally containing additional organic compound, are combined by slurrying or other convenient mixing techniques. Mixing times of at least 30 minutes or more are preferred, and mixing times of about 1 to about 2 hours are particularly preferred.

The treated glass can be dried using any convenient technique. The necessary drying temperature and time will depend in part upon the volatility of the solvent, the surface area of the glass and the manner in which drying is carried out. Drying times can be verified through standard weight loss measurements. Oven drying in a forced air oven is recommended, with overnight drying temperatures of about 30° to 100° C. being preferred.

If desired, the dried silanol-treated fluoroaluminosilicate glass may be further blended with a solution of additional organic compound using any suitable technique (e.g., batch mixing using a double planetary mixer or a twin shell powder mixer). The additional organic compound is presently preferably blended with the dry glass without the addition of solvents, as this avoids the necessity of a second drying step. Solvents may be utilized, however, to facilitate an even distribution of additional treatment. Such solvents can be removed using standard techniques as previously mentioned. Care should be taken to avoid harsh conditions during the drying steps (e.g., excessively high temperatures or prolonged exposure to an oxygen free atmosphere) which might degrade the ethylenically unsaturated double bond of the treatment material.

Following treatment, the glass preferably is screened or lightly comminuted in order to break up agglomerates. The treated glass can be stored as is or, if desired, combined with other adjuvants such as pigments, non-vitreous fillers, inhibitors, accelerators and other ingredients that will be apparent to those skilled in the art.

The treated glass can be made into a cement by combining it in the presence of water with any of the polyacids used in conventional glass ionomer cements. Suitable polyacids include acidic liquids such as those described in U.S. Pat. Nos. 3,814,717 and 4,016,124, and light-cure liquids such as those described in U.S. Pat. Nos. 4,872,936 and 5,063,257 and European Published Pat. Application Nos. 0 323 120 and 0 329 268.

The treated glass preferably retains the ability to release clinically useful aamounts of fluoride ion when made into a cured cement by mixing with an appropriate polyalkenoic acid (e.g., aqueous polyacrylic acid). Fluoride release can conveniently be measured using the procedure set out in EXAMPLE 19 of European Published Pat. Application No. 0 323 120. When so measured, the silanol treated glass preferably has a greater fluoride release than a comparison glass treated with a silane treatment solution.

In order to provide light cure capability, glass ionomer cements made from the treated glass preferably include a free radical initiator, e.g., a photoinitiator. Suitable photoinitiators are described in European Published Pat. Application No. 0 323 120. The cement can contain adjuvants such as viscosity modifiers, ethylenically-unsaturated resins, suffactants, and other ingredients that will be apparent to those skilled in the art.

Glass ionomer cements made from treated glasses of the invention are mixed and clinically applied using conventional techniques. However, the cements will have particular utility in clinical applications where conventional glass ionomer cements typically have been deficient. Such areas include high-stress applications such as restoratives (e.g., posterior tooth restoration, incisal edge replication and bulk dentin replacement), and crown core build-ups.

The invention is further described in the following illustrative examples, which should not be construed as limiting the scope of the invention. Unless otherwise indicated, all parts and percentages are on a weight basis.

PREPARATORY EXAMPLE 1

Monomeric Ethylenically-Unsaturated Acidic Alkoxysilane

A solution of 13 parts itaconic acid in 88.6 parts dry tetrahydrofuran (THF) was placed in a glass reaction vessel equipped with a reflux condenser, drying tube, addition port and stirrer. Next, 0.1 parts dibutyltin dilaurate (DBTDL) and 0.06 pans butylated hydroxytoluene (BHT) were added to the reaction vessel. The temperature was raised to 45° C. Over a 65 minute period, 24.7 pans 3-isocyanatopropyltriethoxysilane (IPTES) were added dropwise to the reaction mixture. The reaction mixture was stirred for 16 hours at 45° C. Examination by infrared spectroscopy (IR) showed that the isocyanato peak at 2250 cm$^{-1}$ had virtually disappeared. THF was removed by rotary evaporation using an air bleed. A small amount of solid separated out and was removed by filtration. The filtrate was analyzed by IR and determined to be a mixture of the following isomers:

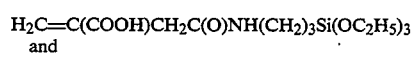
and

IR data: COOH, 1729 cm$^{-1}$; C=C(C))H, 1602 cm$^{-1}$; C=CCH$_2$COOH, 1630 cm$^{-1}$; SiOC$_2$H$_5$, 972 and 1114 cm$^{-1}$; and C(O)NH, 1582 cm$^{-1}$.

PREPARATORY EXAMPLE 2

Ethylenically-Unsaturated Acidic Copolymer

A glass reaction vessel like that used in PREPARATORY EXAMPLE 1 (but having two addition pore) was charged with 132.9 parts THF. One addition port was charged with an acid solution containing 58.6 parts acrylic acid and 26.0 parts itaconic acid in 150.6 parts THF. The other addition port was charged with an initiator solution containing 0.82 parts azobisisobutyronitrile (AIBN) in 115 parts THF. The reaction vessel was flushed with nitrogen and hated to about 60° C. with mechanical sting. The acid solution was added at a rate of about 9 pans every 15 minutes and the initiator solution was added at a rate of about 4.5 parts every 15 minutes. The temperature of the reaction vessel was kept at about 62°-64° C. After addition of the acid and initiator solutions was complete, the reaction mixture was stirred at about 64° C. for 17 hours. IR analysis showed that the ethylenically-unsaturated groups of the starting acids had virtually disappeared, and that the polymerization reaction was complete.

The reaction mixture was allowed to cool to about 35° C. A mixture of 0.15 parts BHT, 0.15 parts triphenylstibene (TPS) and 1.03 parts DBTDL was added to the reaction vessel. A stream of air was introduced into the reaction mixture and the temperature was increased to about 40° C. A solution of 35.34 parts 2-isocyanatoethyl methacrylate (IEM) in 22 parts THF was added dropwise over a period of about 1.5 hours. The reaction mixture was stirred at about 40° C. for an additional hour, followed by stirring at about 20° C. for 18 hours. The reaction mixture was concentrated under vacuum to a syrupy consistency. It was then precipitated into five times its volume of ethyl acetate. The resulting precipitate was filtered, washed with ethyl acetate and dried under vacuum with an air bleed. The polymer yield was 98%, based on the starting amounts of acrylic acid, itaconic acid and IEM. About 10% of the carboxylic acid groups of the polymer reacted with the IEM. The resulting ethylenically-unsaturated acidic copolymer had the following structure:

where R and R' are independently H, COOH or $CH_2COOH$.

PREPARATORY EXAMPLES 3-5

Polymeric Ethylenically-Unsaturated Acidic Alkoxysilanes

The copolymer of PREPARATORY EXAMPLE 2 was reacted with an isocyanate-functional alkoxysilane by dissolving 10.59 parts of the copolymer in 44.3 parts dry THF. Next, solutions of varying amounts of IPTES and 0.02 parts DBTDL in 4.43 parts THF were added to the reaction vessel. Each reaction mixture was stirred for 18 hours at 40° C. IR analysis showed the virtual disappearance of the isocyanato peak. The desired products were precipitated in 226 parts ethyl acetate, filtered and dried under vacuum. The nominal compositions of the resulting polymeric ethylenically-unsaturated acidic silanes are set out below in Table I.

TABLE I

| Preparatory Example | IPTES, Parts | mole % in copolymer COOH | mole % in copolymer $Si(OC_2H_5)_3$ | mole % in copolymer C=C |
|---|---|---|---|---|
| 3 | 1.31 | 81.8 | 4.2 | 16 |
| 4 | 2.47 | 75.6 | 8.4 | 16 |
| 5 | 3.75 | 71.4 | 12.6 | 16 |

IR data: COOH, 1730 cm$^{-1}$; C=C, 1620 cm$^{-1}$; Si-OC$_2$H$_5$, 960 and 1120 cm$^{-1}$ and C(O)NH, 1530 cm$^{-1}$.

PREPARATORY EXAMPLES 6-8

Untreated Fluoroaluminosilicate Glasses

The ingredients set out below in Table II were mixed, melted in an arc furnace at about 1350°-1450° C., poured from the furnace in a thin stream and quenched using chilled rollers to provide amorphous single-phase fluoroaluminosilicate glasses.

TABLE II

| Ingredient | Preparatory Ex. 6, parts | Preparatory Ex. 7, parts | Preparatory Ex. 8, parts |
|---|---|---|---|
| $SiO_2$ | 37 | 37 | 37 |
| $AlF_3$ | 23 | 23 | 23 |
| SrO | 20 | 0 | 20 |
| $CaF_2$ | 0 | 20 | 0 |
| $Al_2O_3$ | 10 | 10 | 10 |
| $AlPO_4$ | 7 | 0 | 0 |
| $Na_3AlF_6$ | 6 | 6 | 6 |
| $P_2O_5$ | 4 | 0 | 4 |

The glasses of PREPARATORY EXAMPLES 6, 7 and 8 were ball-milled to provide pulverized frits with surface areas of 2.6, 3.3 and 2.7 m$^2$/g respectively, measured using the Brunauer, Emmet and Teller (BET) method.

PREPARATORY EXAMPLE 9

Treated Nonreactive Filler 25.5 Parts silica sol ("LUDOX" LS, E.I. duPont de Nemours & Co.) were acidified by the rapid addition of 0.255 parts concentrated nitric acid. In a separate vessel, 12.9 parts ion-exchanged zirconyl acetate (Magnesium Elektron Inc.) were diluted with 20 parts deionized water and the resultant solution acidified with 0.255 parts concentrated nitric acid. The silica sol was pumped into the stirred zirconyl acetate solution and mixed for one hour while filtering the stirred mixture through "CUNO" 5 micrometer and 1 micrometer filters (Commercial Intertech Corp.). The stirred, filtered mixture was further faltered through a 1 micrometer "HYTREX" falter (Osmonics, Inc.) followed by a 0.22 micrometer "BALSTON" falter (Balston Inc.). The filtrate was poured into trays to a depth of about 25 mm and dried at 65° C. in a forced air oven for about 24 hours. The resulting dried material was removed from the oven and tumbled through a rotary tube furnace (Harper Furnace Corporation) preheated to 600° C. 21 Parts of calcined microparticles were obtained. The calcined microparticles were comminuted in a tumbling ball mill until all of the microparticles were less than 10 micrometers in particle diameter. 0.3 Part portions of the milled microparticles were placed in ceramic saggers and fired in an electric kiln (Harper Furnace Corporation) in air at 825° C. for 1 hour. The fired microparticles were allowed to cool in air. The cooled microparticles were slurried in hydrolyzed gamma-methacryloxypropyl trimethoxysilane ("A-174", Union Carbide Corp.), dried in a forced air oven and screened through a 74 micrometer screen. The treated filler particles contained 11.1% silane.

COMPARATIVE EXAMPLE 1

Using the general procedure outlined in Examples 6 and 7 of the '257 patent (with some minor variations not believed to affect the result), a silane-treated glass, cement solution and cement were prepared as follows:

Using a yellow safelight, the glass of PREPARATORY EXAMPLE 6 was screened through a 74 micron mesh sieve. 100 Parts of the glass powders were mixed in a beaker with 20 pans of a 10% solution of A-174 in ethanol to treat the glass with the silane. The mixture was heated at 110° C. for 2 hours over a steam dryer. 100 Parts of the silane-treated powders were mixed in a mortar with 1 part dimethylaminoethyl methacrylate (DMAEM).

30 Parts of a 4:1 acrylic acid:itaconic acid copolymer having an average molecular weight ($\overline{M}_w$) of about 17,500 (measured using gel permeation chromatography (GPC) with THF as the GPC solvent, and evaluated against a polystyrene standard), were combined with 30 parts 2,2'-bis[3-(4-phenoxy)-2-hydroxypropane-1-methacrylate]propane, 10 parts di-2-methacryloxyethyltetramethylene dicarbamate, 30 parts distilled water, 1.5 parts polyoxyethylene sorbitan monooleate ester and 0.5 parts polyoxyethylene sorbitan monostearate ester. The ingredients were mixed for 4.5 hours using a paint shaker. The resulting aqueous cement solution was cloudy and thus not completely homogenous. 0.25 Parts camphorquinone (CPQ) and 0.05 parts BHT were added to the solution.

The silane-treated powder and the cement solution were mixed for 1 minute using a 2.6:1 powder:liquid (P:L) ratio. The resulting cement was packed into a 4 mm inside diameter glass tube, capped with silicone rubber plugs, and axially compressed at about 0.28 MPa. About 1.5 minutes after the start of mixing, the sample was exposed for 80 seconds to light from two oppositely-disposed visible light curing lamps ("VISI-LUX2" curing lamp, 3M). Five cured samples were evaluated to determine the avenge compressive strength (CS) and DTS, using the measurement methods described in EXAMPLE 14 of European Published Pat. Application No. 0 323 120. An average CS of 130 MPa and an average DTS of 14.3 MPa were obtained. The cement was evaluated for fluoride release using the measurement method set out in EXAMPLE 19 of European Published Pat. Application No. 0 323 120. The results for the fluoride release measurement are set out below in EXAMPLE 1.

EXAMPLE 1

The procedure of COMPARATIVE EXAMPLE 1 was repeated, but the glass powder was treated using the method of the present invention. 100 Parts of the untreated glass powder of PREPARATORY EXAMPLE 6 were mixed with an aqueous, acidic silanol solution prepared by combining 2.08 parts A-174 silane, 25.3 parts methanol and 24 parts water, acidifying the solution to pH 3.5 using trifluoroacetic acid (TFA) and stirring for one hour. IR analysis established the presence of a peak at about 3510 cm$^{-1}$, indicative of the presence of a silanol group. This peak was not present in the silane treating solution of COMPARATIVE EXAMPLE 1.

The glass powder and silanol solution were stirred together for 4.25 hours, then dried overnight in a 45° C. oven. The treated glass powder was sieved through a 74 micron mesh screen. Analysis by DRIFT established the presence of peaks centered at about 1550 to 1610 cm$^{-1}$, indicative of the presence of carboxylate ions. These peaks were not present in the treated glass of COMPARATIVE EXAMPLE 1.

When mixed at a 2.6:1 P:L ratio and evaluated using the method of COMPARATIVE EXAMPLE 1, cements with an average CS of 152 MPa and an average DTS of 29 MPa were obtained. Although the only difference in procedure for this example (vs. COMPARATIVE EXAMPLE 1) was the use of an aqueous acidic silanol treating solution (rather than an anhydrous alkoxysilane treating solution), the observed DTS was two times higher than mat of COMPARATIVE EXAMPLE 1.

The cement of the invention was evaluated for fluoride release and compared to the cement of COMPARATIVE EXAMPLE 1. The results were as follows:

TABLE III

| | Cumulative fluoride release, µg/g | |
|---|---|---|
| Days | COMPARATIVE EXAMPLE 1 | EXAMPLE 1 |
| 0 | 3.0 | 13.2 |
| 12 | 51.8 | 362.0 |
| 32 | 59.7 | 726.0 |
| 41 | 69.4 | 756.1 |
| 84 | 170.4 | 1100.4 |

The cement of the invention exhibited much greater fluoride release than the comparison cement.

EXAMPLES 2–16

For EXAMPLES 2–5, the procedure of EXAMPLE 1 was repeated using the glass of PREPARATORY EXAMPLE 6. The treatment solutions employed "A-174" silane, methanol, water and TFA. Cement test samples were formed by combining the treated glasses at a 1.4:1 P:L ratio with Liquid A in Table IV.

The treatment solution of EXAMPLE 6 was prepared by mixing A-174 silane and water, adjusting the pH of the solution to 3.01 with acetic acid and stirring for one-half hour. The glass of PREPARATORY EXAMPLE 8, but with a surface area of 2.8 m$^2$/g instead of 2.7 m$^2$/g, was mixed with the treating solution. An additional 15 pans water was added and the glass powder and silanol solution were stirred for 1.5 hours. The treated glass was dried overnight in a 45° C. oven and then sieved through a 74 micron mesh screen. Cement test samples were formed by combining the treated glass at a 2.2:1 P:L ratio with Liquid B in Table IV.

The treatment solution of EXAMPLE 7 was prepared by mixing A-174 silane and water, adjusting the pH of the solution to 10.03 with a 10% sodium hydroxide solution and stirring for one hour. The glass of PREPARATORY EXAMPLE 8 was mixed with the treating solution, dried at 30° C. for 2.5 days and ground to a fine powder using a mortar and pestle. Cement test samples were formed by combining the treated glasses at a 2.2:1 P:L ratio with Liquid B in Table IV.

The treatment solutions of EXAMPLES 8–11 were prepared by mixing the ionic silanes listed in Table V in water and adjusting the pH of the solution with TFA and stirring for one hour. The glass of PREPARA- TORY EXAMPLE 8 was independently mixed with each treating solution, dried at 30° C. for 2.5 days and ground to a fine powder using a mortar and pestle. Cement test samples were formed by combining each of the treated glasses at a 2.2:1 P:L milo with Liquid B in Table IV.

The treatment solution of EXAMPLE 12 employed the acidic monomeric silane of PREPARATORY EXAMPLE 1, ethanol and water. No other acid addition was required. The glass of PREPARATORY EXAMPLE 6 was mixed with the treating solution and dried as described for EXAMPLE 1. Cement test samples were formed by combining the treated glasses at a 1.4:1 P:L ratio with Liquid A in Table IV.

The treatment solutions of EXAMPLES 13–16 employed the acidic polymeric silane of PREPARATORY EXAMPLE 3, ethanol and water. No other acid addition was required. The glass of PREPARATORY EXAMPLE 6 was independently mixed with each treating solution and dried as described for EXAMPLE 1. Cement test samples were formed by combining the treated glasses at a 1.4:1 P:L ratio with Liquid A in Table IV.

A cement composition ("Control A") made from untreated glass was prepared and evaluated as a control. A further control composition ("Control B") was prepared by treating 100 pans glass with a treatment solution containing 4 parts of the dry copolymer of PREPARATORY EXAMPLE 5 (viz., a copolymer without alkoxysilane groups), 25.1 parts ethanol and 80 parts water. A final control composition ("Control C") was prepared by treating the glass with a treatment solution containing 4 parts of a 4:1 acrylic acid:itaconic acid copolymer (made by extracting and drying a portion of the reaction mixture of PREPARATORY EXAMPLE 2 before the BHT, TPS, DBTDL and IEM were added), 25.1 pans ethanol and 80 parts water.

Cement test samples were prepared by combining the treated glasses with a cement-forming copolymer solution made by mixing the ingredients set out below in Table IV.

TABLE IV

| Ingredients | Liquid A, Parts | Liquid B, Parts |
|---|---|---|
| Dry copolymer of PREP. EXAMPLE 2 | 50 | 50 |
| Water | 30 | 30 |
| 2-Hydroxyethyl methacrylate | 20 | 20 |
| Diphenyliodonium chloride | 2.5 | 0 |
| Diphenyliodonium hexafluorophosphate | 0 | 1.0 |
| CPQ | 0.5 | 0.25 |
| BHT | 0 | 0.05 |

Set out below in Table V are the example number, the type of silane, the silane:alcohol:water:glass ratio, the pH of the silanol treatment solution, the weight percent silanol on the glass (based on the weight of the starting materials, without accounting for the lost weight of alkoxy groups in the hydrolyzed silane or the lost weight of water produced by condensation of the silanol on the glass surface), and the CS and DTS for the final cements.

TABLE V

| Ex. No. | Silane | Silane:alcohol: water:glass ratio | pH | Wt % silanol | CS MPa | DTS, MPa |
|---|---|---|---|---|---|---|
| 2 | A-174 | 0.6:18.8:16:100 | 3.5 | 0.6 | 156 | 29 |
| 3 | A-174 | 2:25.2:24:100 | 3.5 | 2 | 172 | 31 |
| 4 | A-174 | 4:25:25:100 | 3.45 | 4 | 207 | 31 |
| 5 | A-174 | 8:41.2:12:100 | 3.1 | 8 | 168 | 33 |
| 6 | A-174 | 4:0:40:100 | 3.01 | 4 | 223 | 34 |
| 7 | A-174 | 3.8:0:100:100 | 10.03 | 3.8 | 134 | 17 |
| 8 | T2909.7 | 4.6:4.6:100:100 | 3.05 | 4.6 | 136 | 24 |
| 9 | T2921 | 4.6:0:100:100 | 3.05 | 4.1 | 125 | 17 |
| 10 | T2924 | 8.1:8.1:100:100 | 3.05 | 8.1 | 132 | 16 |
| 11 | T2925 | 3.6:3.6:100:100 | 3.05 | 3.6 | 119 | 16 |
| 12 | P.E.1[1] | 4:25.1:80:100 | 3.2 | 4 | 140 | 31 |
| 13 | P.E.3[2] | 2:25.1:80:100 | 3.1 | 2 | 152 | 30 |
| 14 | P.E.3 | 4:25.1:80:100 | 3.2 | 4 | 154 | 31 |
| 15 | P.E.3 | 4:25.6:48:100 | 3.35 | 4 | 176 | 26 |
| 16 | P.E.3 | 8:25.1:80:100 | 3.2 | 8 | 147 | 24 |
| Ct. A | None | N.A.[3] | N.A. | 0 | 143 | 15 |
| Ct. B[4] | None | 0:25.1:80:100 | 2.9 | 0 | 142 | 14 |
| Ct. C[5] | None | 0:25.1:80:100 | 1.6 | 0 | 136 | 18 |

[1]"P.E.1" = Monomeric silane of PREPARATORY EXAMPLE 1.
[2]"P.E.3" = Polymeric silane of PREPARATORY EXAMPLE 3.
[3]Not applicable (no treatment).
[4]Treated with a treatment solution containing 4 parts of the silane-free dry copolymer of PREPARATORY EXAMPLE 5 per 100 parts of glass.
[5]Treated with a treatment solution containing a 4:1 acrylic acid:itaconic acid copolymer that did not contain ethylenic unsaturation or alkoxysilane groups.

The data shown above illustrate the significant increases in DTS provided by the invention. For example, the Control A cement had a DTS of 15 MPa, while in many cases the cements of the invention had DTS values that were 1.6 to 2.2 times higher (24 to 33 MPa). The cements of the invention would therefore be much better suited to high stress applications.

The cements of the invention also had higher DTS values than those obtained for the Control B and Control C cements. This demonstrated that the improved DTS values were not due merely to the use of treating solutions containing ethylenically-unsaturated copolymers or acidic copolymers.

The cements of EXAMPLES 7–11 and Control A were evaluated for fluoride release on day 0 and after 12 days using the measurement method set out in EXAMPLE 19 of European Published Pat. Application No. 0 323 120 and compared to the cement of COMPARATIVE EXAMPLE 1. The results are provided in Table VI.

TABLE VI

| EXAMPLE | Cumulative fluoride release, μg/g | |
|---|---|---|
|  | Day 0 | Day 12 |
| COMPARATIVE EX. 1 | 3.0 | 51.8 |
| Control A | 19.0 | 350.0 |
| 7 | 8.1 | 214.7 |
| 8 | 27.9 | 259.9 |
| 9 | 13.9 | 211.4 |
| 10 | 19.6 | 359.6 |
| 11 | 21.3 | 285.4 |

The cements of the invention exhibited much greater fluoride release than the comparison cement.

EXAMPLE 17

The procedure of EXAMPLE 14 was repeated using a glass with a 3.6 m²/g surface area. The treated glass was mixed with a copolymer solution like that of Liquid A in Table IV, but made from a different copolymer. The copolymer was made like the copolymer of PREPARATORY EXAMPLE 5, but using a 2:3 molar ratio of acrylic acid:itaconic acid (which formed a copolymer having a $\overline{M}_w$ of 9,450 by GPC), and reacting 34% of the copolymer's carboxylic acid groups with IEM. Cements made using the resulting copolymer solution at a 1.4:1 P:L ratio had a CS of 170 MPa and a DTS of 31 MPa.

EXAMPLES 18–22

The procedure of EXAMPLES 2–5 was repeated, using the glass of PREPARATORY EXAMPLE 7. Different treating solutions were employed, along with an untreated control.

The treatment solutions of EXAMPLES 18, 19 and 20 employed the polymeric nonionic alkoxysilane of PREPARATORY EXAMPLE 3, methanol and water. No other acid addition was required. The treatment solution of EXAMPLE 21 employed the polymeric nonionic alkoxysilane of PREPARATORY EXAMPLE 4, ethanol and water. Again, no other acid addition was required. The treatment solution of EXAMPLE 22 employed the polymeric nonionic alkoxysilane of PREPARATORY EXAMPLE 3, ethanol and water. Again, no other acid addition was required. The control composition ("Control D") contained untreated glass. The cement-forming copolymer solution was Liquid A in Table IV.

Set out below in Table VII are the example number, the type of silane, the silane:alcohol:water:glass ratio, the pH of the silanol treatment solution, the weight percent silanol on the glass, and the CS and DTS for the final cements.

TABLE VII

| Ex. No. | Silane | Silane:alcohol: water:glass ratio | pH | Wt % silanol | CS, MPa | DTS, MPa |
|---|---|---|---|---|---|---|
| 18 | P.E.3[1] | 2:25.1:100:100 | 4.2 | 2 | 156 | 28 |
| 19 | P.E.3 | 4:25.1:100:100 | 3.2 | 4 | 172 | 34 |
| 20 | P.E.4[2] | 4:50.2:16:100 | 3.2 | 4 | 164 | 31 |
| 21 | P.E.3 | 6:25.1:100:100 | 3.2 | 6 | 173 | 31 |
| 22 | P.E.3 | 12:50.2:80:100 | 3.4 | 12 | 132 | 23 |
| Control D | None | N.A | N/A | 0 | 164 | 21 |

[1]"P.E.3" = Polymeric nonionic alkoxysilane of PREPARATORY EXAMPLE 3.
[2]"P.E.4" = Polymeric nonionic alkoxysilane of PREPARATORY EXAMPLE 4.

The data shown above further illustrate the significant DTS improvement provided by the invention. Cements made from a glass treated using the method of the invention had higher DTS values than the Control D cement.

EXAMPLE 23

The ingredients set out below in Table VIII were mixed together and stirred magnetically for 30 minutes at ambient temperature.

TABLE VIII

| Ingredient | Parts |
|---|---|
| A-174 silane | 2.0 |
| methanol | 12.6 |
| water | 12.5 |
| acetic acid | 0.22 |

The mixture was added to 50.02 parts of a glass powder like that of PREPARATORY EXAMPLE 6 (but having a surface area of 2.8 m$^2$/g) and slurried for 1.5 hours at ambient temperature. The slurry was then poured into a plastic-lined tray and dried for 20 hours at 45° C. The dried powder was sieved through a 74 micron mesh screen.

A DRIFT spectrum of the treated powder showed absorbance peaks at 2953, 2932, 2892, 1719, 1696, 1636, 1580, 1452 and 1400 cm$^{-1}$. The last three peaks indicate the presence of carboxylate ions.

A cement mixture was formed by spatulating 2.2 parts of the treated powder with 1.0 part of a liquid like Liquid A in Table IV (but with 1.0 part diphenyliodonium hexafluorophosphate rather than 2.5 parts diphenyliodonium chloride). The cement had a CS of 210 MPa and a DTS of 30 MPa. The cement had an excellent balance of physical properties and aesthetics.

EXAMPLE 24

Modification of a Commercial Fluoroaluminosilicate Glass

In a series of four runs, "VITREBOND" Glass Ionomer Liner/Base (3M) glass powder (surface area of 2.2–2.5 m$^2$/g) was independently treated with varying concentrations of a silanol treatment solution. The silanol treatment solutions were prepared by independently adding 0.0072 parts, 0.036 parts, 0.054 parts and 0.259 parts A-1100 silane to 12 parts deionized water to form treatment solutions of 0.1%, 0.5 %, 1.0% and 5.0% silanol respectively. The pH of the solutions was 10.8. No base addition was required. After stirring for 30 minutes, 5 parts VITREBOND glass powder was added to each solution. Each treated glass was allowed to air dry and was ground to a fine powder using a mortar and pestle. Cements were prepared by independently mixing the treated glasses at a 1.4:1 P:L ratio with a cement-forming copolymer solution made by mixing the ingredients set out below in Table IX.

TABLE IX

| Ingredients | Parts |
|---|---|
| Dry copolymer of PREPARATORY EXAMPLE 2 | 40 |
| Water | 36 |
| 2-Hydroxyethyl methacrylate | 24 |
| CPQ | 0.5 |
| BHT | 0.05 |

As a comparison, a cement composition ("Control E") was made by mixing at the same P:L ratio untreated VITREBOND glass powder and the cement-forming liquid of Table IX. Set out below in Table X are the run no., the weight % A-1100 silane and the CS and DTS for the final cements.

TABLE X

| Run No. | Wt. % Silane | CS, MPa | DTS, MPa |
|---|---|---|---|
| 1 | 0.1 | 89 | 19 |
| 2 | 0.5 | 80 | 10 |
| 3 | 1.0 | 63 | 6 |
| 4 | 5.0 | 72 | 13 |
| Control E | 0 | 63 | 12 |

The data in Table X illustrate the significant improvement in physical properties provided by addition of a small amount of silanol to the glass (Run no. 1). As greater amounts of silanol were added to the glass (Run nos. 2–4), working time greatly decreased making it very difficult to obtain accurate physical property determinations.

EXAMPLE 25

Treated Fluoroaluminosilicate Glass

To 2.0 pans A-174 silane was added 12.6 parts methanol, 12.6 parts water and 0.22 parts acetic acid. The ingredients were mixed together and stirred magnetically for 30 minutes at ambient temperature. The mixture was added to 50 parts of a glass powder like that of PREPARATORY EXAMPLE 8 and slurried for 1.5 hours at ambient temperature. The slurry was then poured into a plastic-lined tray and dried for 20 hours at 45° C. The dried powder was sieved through a 74 micron mesh screen.

EXAMPLES 26-42

The glasses of PREPARATORY EXAMPLE 8 and EXAMPLE 25 and the filler of PREPARATORY EXAMPLE 9 were treated with one or more additional organic compounds as listed in Table XI. The treatments were applied by mixing neat solutions (i.e., without the aid of a volatile solvent) of the additional organic compound or compounds with the glass or filler until the glass or filler was uniformly coated. With the exception of Examples 41 and 42 the treated glass or filler was essentially a dry powder after the treatment solution was applied. In contrast, Examples 41 and 42 were coated with sufficient additional organic compound such that the resultant mixture was no longer a powder but rather a viscous paste.

Cement test samples were prepared by combining the treated glasses and fillers with a cement-forming copolymer solution (Liquid B of Table IV). The relative weight ratio of additional organic compound, glass, filler and liquid is listed in Table XI for each example. Also set out below in Table XI are the example number, the type of additional coating or coatings and the value of the CS, DTS and fracture toughness ("$K_{1c}$") of each example. The experimental values for CS, DTS and $K_{1c}$ represent the mean value of at least 5 experimental runs The fracture toughness of the cement test samples was measured using the short rod specimen geometry. This test is presently believed to measure the resistance of a dental restorative material (e.g., a dental cement or composite) to crack propagation. The samples of this invention were tested in the manner described by L. M. Barker in a research article entitled: "Compliance Calibration of a Family of Short Rod and Short Bar Fracture Toughness Specimens," *Engineering Fracture Mechanics* Vol. 17, No. 4, pp. 289-312, 1983.

The test sample geometry of the short rod specimen is illustrated in FIG. 1(a) on page 291 of the Barker article. The specimens of the present invention follow this geometry with the following deviations. The test samples were molded into 4 mm diameter cylinders of 8 mm length and then notched as illustrated in FIG. 1(a) using diamond cutting saws. Therefore, referring to the table accompanying FIG. 1(a): "B" is 4 mm, "L" is 8 mm, "$1_o$" is 4 mm and "$\tau$" is 150 microns for the specimens of this invention. In addition the loadline is 2 mm from the edge of the sample and the chevron angle "$\theta$" is 56°.

The fracture toughness of the cements were calculated using the following equation:

$$K_{1c} = f(1/B)(F/B^{1.5})$$ (equation 3 from Barker)

where "F" is the failure load, "B" is the specimen diameter and "f(1/B)" represents the stress intensity factor coefficient. The stress intensity factor coefficient is calculated using equation (6) of the Barker reference and was experimentally determined to be 24.83 for the specimens of this invention.

TABLE XI

| Ex. | Table IV Liq. B Parts | Example 25 Parts | Prep Ex. 8 Parts | Prep Ex. 9 Parts | Additional Organic Compound(s) (Parts) | CS, MPa | DTS, MPa | $K_{1C}$, MN/m$^{1.5}$ |
|---|---|---|---|---|---|---|---|---|
| F | 12.5 | — | 75 | — | — | 63 | 12 | 0.87 |
| G | 12.5 | — | — | 75 | (12.5) PEG$_{200}$DMA | 210 | 15 | 0.49 |
| H | 12.5 | 75 | — | — | (12.5) TEG | 54 | 9 | — |
| 26 | 12.5 | 71 | — | — | — | 214 | 16 | 0.81 |
| 27 | 12.5 | — | 75 | — | (12.5) PEG$_{200}$DMA | 155 | 20 | 0.90 |
| 28 | 12.5 | 75 | — | — | (12.5) PEG$_{200}$DMA | 222 | 32 | 1.00 |
| 29 | 12.5 | 52.5 | — | 22.5 | (12.5) PEG$_{200}$DMA | 215 | 26 | — |
| 30 | 12.5 | 37.5 | — | 37.5 | (12.5) PEG$_{200}$DMA | 253 | 38 | 0.86 |
| 31 | 12.5 | 75 | — | — | (12.5) PEG$_{400}$DMA | 112 | 14 | 0.65 |
| 32 | 12.5 | 75 | — | — | (12.5) PEG$_{600}$DMA | 141 | 16 | 0.57 |
| 33 | 12.5 | 75 | — | — | (12.5) TEGDMA | 223 | 34 | — |
| 34 | 9.0 | 75 | — | — | (16.0) TEGDMA/PC[1] | 249 | 29 | 0.97 |
| 35 | 12.5 | 75 | — | — | (6.25) PEG$_{200}$DMA (6.25) BIS-GMA | 262 | 31 | 1.08 |
| 36 | 12.5 | 75 | — | — | (6.25) PEG$_{200}$DMA (6.25) BIS-GMA | 249 | 28 | — |
| 37 | 12.5 | 75 | — | — | (8.75) PEG$_{200}$DMA (3.75) TAGU | 230 | 21 | |
| 38 | 12.5 | 37.5 | — | 3.75 | (6.25) PEG$_{200}$DMA (6.25) BIS-GMA | 276 | 38 | 1.16 |
| 39 | 12.5 | 75.0 | — | — | (12.5) SR350 | 221 | 33 | 0.50 |
| 40 | 8.0 | 36.0 | — | 36.0 | (8) PEG$_{200}$DMA (10) BIS-GMA (2) Glyceroldimethacrylate | 293 | 49 | 1.23 |
| 41 | 8.0 | 48.0 | — | 24.0 | (8) PEG$_{200}$DMA (10) BIS-GMA (2) Glyceroldimethacrylate | 273 | 47 | 1.21 |
| 42 | 8.0 | 72.0 | — | — | (10) PEG$_{200}$DMA (10) BIS-GMA | 241 | 39 | 1.10 |

[1]Triethylene glycol dimethacrylate saturated with "Calibre 300" grade polycarbonate, available from Dow Chemical Co.

The data shown above illustrate the significant increases in CS, DTS and $K_{1c}$ provided by the treatments of the present invention. For example, control EXAMPLE F (using untreated fluoraluminosilcate glass and no additional organic coating) and EXAMPLE 26 (using silanol treated fluoroaluminosilicate glass and no additional organic compound treatment) had CS values of 63 and 214 MPa respectively. Cements of the present invention which had both a silanol coating and an additional organic compound treatment, e.g., EXAMPLE 40, had CS values of up to 293 MPa. The $K_{1c}$ value of the untreated control, EXAMPLE F, was 0.87 MN/m$^{1.5}$, while in many cases cements of the present invention which had both a silanol coating and an additional organic compound treatment had $K_{1c}$ values up to 1.4 times higher (1.23 MN/m$^{1.5}$). Likewise the DTS of the cements of the present invention are two to four times the value of the untreated control.

EXAMPLE 27 illustrates the improvement which can be obtained using glasses that contain the additional organic compound treatment but do not contain the silanol treatment of the present invention. A direct comparison of EXAMPLE 27 and control EXAMPLE F illustrates the advantages of the additional organic coating when no silanol treatment is applied (CS is increased from 63 MPa to 155 MPa; while the DTS and $K_{1c}$ values show a more modest increase).

Control EXAMPLE G illustrates the utility of further treating silanol treated non reactive filler particles with an additional organic compound. While the CS and DTS values of this control are quite respectable (210 and 15 MPa respectively), the fracture toughness value is relatively low (0.49 MN/m$^{1.5}$). This is believed to be due to the inability of the non-reactive filler to participate in the cement reaction with Liquid B. When this same filler is mixed with a reactive glass (e.g., the glass of either PREPARATORY EXAMPLE 8 or EXAMPLE 25) the CS, DTS and fracture toughness improve. EXAMPLES 29, 30, 38, 40 and 41 exemplify this combination.

Control EXAMPLE H illustrates the effect of coating a silanol treated fluoroaluminosilcate glass with a triethyleneglycol ("TEG") compound. This compound differs from the solutions of the present invention in that it is incapable of further polymerization (i.e., TEG is incapable of participating in either the cement reaction or a hardening reaction with the other monomers or polymers of the cement composition). Control EXAMPLE H has a lower CS and DTS values than a cement using an untreated glass.

Although this invention has been described using certain illustrative examples, it should be understood that the invention is not limited to the specific exemplary embodiments shown in this specification.

We claim:

1. A method for treating fluoroaluminosilicate glass, comprising the steps of:
    a. mixing finely-divided fluoroaluminosilicate glass with an aqueous silanol solution, and
    b. drying the glass, said glass being capable of forming a cement when mixed with water and a polyalkenoic acid.

2. A method according to claim 1, wherein the silanol is ionic and at least 0.1 percent hydrolyzed.

3. A method according to claim 1, wherein the silanol is nonionic and at least 0.1 percent hydrolyzed.

4. A method according to claim 1, wherein the solution is acidic and the silanol is ethylenically-unsaturated.

5. A method according to claim 1, wherein the solution is basic and the silanol is ethylenically-unsaturated.

6. A method according to claim 1, wherein the solution is acidic and the acid is borne on the silanol.

7. A method according to claim 1, wherein the solution is acidic and the acid is borne on the silane from which the silanol is formed.

8. A method according to claim 1, wherein the solution is basic and the base is borne on the silanol.

9. A method according to claim 1, wherein the solution is basic and the base is borne on the silane from which the silanol is formed.

10. A method according to claim 1, wherein the silanol has one or more pendant carboxylic acid groups.

11. A method according to claim 1, wherein the silanol has the formula $R_nSi(OH)_{4-n}$ wherein R is a non-hydrolyzable polymerizable organic group and n is one to three.

12. A method according to claim 1, wherein the silanol was formed by hydrolysis of the alkoxy groups of an ethylenically-unsaturated alkoxysilane of the formula:

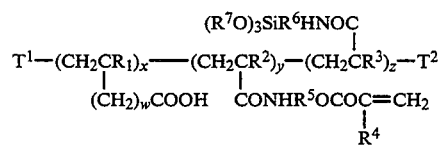

wherein $R^1$, $R^2$, $R^3$ and $R^4$ are independently H, $CH_3$, COOH or $CH_2COOH$; $R^5$ and $R^6$ are independently divalent alkylene linking groups; each $R^7$ is independently an alkyl group; $T^1$ and $T^2$ are independently terminating groups such as H or alkyl; w is 0 to 12; and each of x, y and z is at least one.

13. A method according to claim 1, wherein the solution is acidic and the acid is present as a separate component of the solution.

14. A method according to claim 1, wherein the solution is basic and the base is present as a separate component of the solution.

15. A method according to claim 13, wherein the acid is selected from the group consisting of formic acid, acetic acid, trifluoroacetic acid, propionic acid, pentafluoropropionic acid, hydrochloric acid, nitric acid, sulfuric acid, phosphoric acid, lactic acid, citric acid and tartaric acid, and said solution further comprises a solvent selected from the group consisting of methanol, ethanol, propanol, isopropanol, tert-butanol and acetone.

16. A method according to claim 14, wherein the base is selected from the group consisting of sodium hydroxide, ammonium hydroxide, potassium hydroxide, barium hydroxide, lithium hydroxide, magnesium hydroxide, calcium hydroxide, sodium bicarbonate, ammonia, methylamine, dimethylamine, trimethylamine, ethylamine, diethylamine, n-propylamine, n-butylamine, isobutylamine, sec-butylamine, and tert-butylamine and said solution further comprises a solvent selected from the group consisting of methanol, ethanol, propanol, isopropanol, tert-butanol and acetone.

17. A method according to claim 1, wherein the solution contains about 0.1 to about 20 weight % silanol and about 80 to about 99.9 weight % water.

18. A method according to claim 1 wherein the glass is further treated with an additional organic compound.

19. A method according to claim 18, wherein the additional organic compound has at least one functional group selected from the group consisting of acrylates and methacrylates.

20. A method according to claim 18, wherein the additional organic compound has a weight avenge molecular weight per double bond of between about 100 and 5000.

21. A method according to claim 18, wherein the additional organic compound comprises polyethyleneglycol dimethacrylate.

22. A method according to claim 18, wherein the silanol solution and the additional organic compound are sequentially applied to the glass.

23. A method according to claim 1, wherein the solution contains about 0.1 to about 20 weight % silanol, at least about 40 weight % volatile solvent, and about 20% to about 60 weight % water.

24. A method according to claim 1, wherein the solution contains about 0.1 to about 10 weight % silanol, water, and sufficient acid to provide a pH of about 1 to about 4.5.

25. A method according to claim 1, wherein the solution contains about 0.1 to about 10 weight % silanol, water, and sufficient base to provide a pH of about 8 to about 12.

26. A method according to claim 1, wherein the dried treated glass a forms a cement upon being mixed with water and a polyacrylic acid, and one day after forming said cement releases fluoride at a rate greater than a like glass having a silane treatment.

27. A method of making a glass ionomer cement, comprising the steps of:
  a. treating finely-divided fluoroaluminosilicate glass with an aqueous silanol solution;
  b. mixing the treated glass with a polyalkenoic acid; and
  c. allowing the mixture of step b) to harden.

28. A method according to claim 27, wherein the solution is acidic and the silanol is ethylenically-unsaturated.

29. A method according to claim 27, wherein the silanol has the formula $R_nSi(OH)_{4-n}$ wherein R is a non-hydrolyzable polymerizable organic group and n is one to three.

30. A method according to claim 27, wherein the silanol was formed by hydrolysis of the alkoxy groups of an ethylenically-unsaturated alkoxysilane of the formula:

$$\begin{array}{c} (R^7O)_3SiR^6HNOC \\ | \\ T^1-(CH_2CR_1)_x-(CH_2CR^2)_y-(CH_2CR^3)_z-T^2 \\ | \quad\quad\quad\quad | \\ (CH_2)_wCOOH \quad CONHR^5OCOC=CH_2 \\ \quad\quad\quad\quad\quad\quad | \\ \quad\quad\quad\quad\quad\quad R^4 \end{array}$$

wherein $R^1$, $R^2$, $R^3$ and $R^4$ are independently H $CH_3$, COOH or $CH_2COOH$; $R^5$ and $R^6$ are independently divalent alkylene linking groups; each $R^7$ is independently an alkyl group; $T^1$ and $T^2$ are independently terminating groups such as H or alkyl; w is 0 to 12; and each of x, y and z is at least one.

31. A method according to claim 27, wherein the solution is acidic and the acid is present as a separate component of the solution.

32. A method according to claim 27, wherein the glass is further treated with an additional organic compound.

33. A method according to claim 32, wherein the additional organic compound has at least one functional group selected from the group consisting of acrylates and methacrylates.

34. A method according to claim 32, wherein the silanol solution and the additional organic compound are sequentially applied to the glass.

35. A method according to claim 27, wherein the solution contains about 0.1 to about 20 weight % silanol, at least about 40 weight % volatile solvent and about 20 to about 60 weight % water.

36. A method according to claim 27, wherein one day after mixing with the polyalkenoic acid the cement releases fluoride at a rate greater than a like glass having a silane treatment.

37. A method according to claim 27, wherein twelve days after mixing with the polyalkenoic acid the cumulative fluoride release rate of the cement is at least 52 μg/g.

* * * * *

UNITED STATES PATENT AND TRADEMARK OFFICE
CERTIFICATE OF CORRECTION

PATENT NO. : 5,332,429
DATED : July 26, 1994
INVENTOR(S) : Sumita B. Mitra, Scott R. Culler, and Bing Wang It is certified that error appears in the above-indentified patent and that said Letters Patent is hereby corrected as shown below:

Column 2, Line 64, delete "fore" and insert --form-- therefore.

Column 3, Lines 24, 25 & 30, delete "home" in all three lines and insert --borne-- therefore.

Column 5, Line 3, delete "polyacrylonitsile" and insert --polyacrylonitrile-- therefore.

Column 6, Line 33, delete "aamounts" and insert --amounts--.

Column 6, Line 52, delete "n-butylamine" and insert --n-butylamine-- therefore.

Column 7, Lines 9 & 11, delete "aamount" in both places and insert --amount-- therefore.

Column 8, Line 6, delete "aamounts" and insert --amounts-- therefore.

Column 8, Line 50, delete "pans" and insert --parts-- therefore.

Column 9, Line 5, delete "pore" and insert --ports-- therefore.

Column 9, Line 12, delete "hated" and insert --heated-- therefore.

Column 9, Line 13, delete "sting" and insert --stirring-- therefore.

Column 9, Line 14, delete "pans" and insert --parts-- therefore.

Column 10, Line 51, delete "faltered" and insert --filtered-- therefore.

Column 10, Line 52 & 53, delete "falter" in both places and insert --filter-- therefore.

Column 11, Line 13, delete "pans" and insert --parts-- therefore.

UNITED STATES PATENT AND TRADEMARK OFFICE
CERTIFICATE OF CORRECTION

PATENT NO. : 5,332,429
DATED : July 26, 1994
INVENTOR(S) : Sumita B. Mitra, Scott R. Culler, and Bing Wang It is certified that error appears in the above-indentified patent and that said Letters Patent is hereby corrected as shown below:

Column 12, Line 17, delete "mat" and insert --that-- therefore.

Column 12, Line 50, delete "pans" and insert --parts-- therefore.

Column 13, Line 5, delete "milo" and insert --ratio-- therefore.

Column 13, Line 27, delete "pans" and insert --parts-- therefore.

Column 16, Line 62, delete "pans" and insert --parts-- therefore.

Column 20, Line 66, delete "avenge" and insert --average-- therefore.

Column 21, Lne 21, delete "a" after the word "glass".

Column 21, Line 22, delete "polyacrylic" and insert --polyalkenoic-- therefore.

Signed and Sealed this

First Day of July, 1997

Attest:

Attesting Officer

BRUCE LEHMAN

Commissioner of Patents and Trademarks